(12) United States Patent
Marrone et al.

(10) Patent No.: US 12,110,264 B2
(45) Date of Patent: Oct. 8, 2024

(54) PROCESS FOR PRODUCING UREA AND BIURET

(71) Applicant: Casale SA, Lugano (CH)

(72) Inventors: Leonardo Marrone, Mercallo (IT); Alberto Benedetti, Como (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 18/267,826

(22) PCT Filed: Nov. 19, 2021

(86) PCT No.: PCT/EP2021/082271
§ 371 (c)(1),
(2) Date: Jun. 16, 2023

(87) PCT Pub. No.: WO2022/128328
PCT Pub. Date: Jun. 23, 2022

(65) Prior Publication Data
US 2024/0043375 A1   Feb. 8, 2024

(30) Foreign Application Priority Data

Dec. 16, 2020 (EP) .................................... 20214560

(51) Int. Cl.
*C07C 273/16* (2006.01)

(52) U.S. Cl.
CPC .................................. *C07C 273/16* (2013.01)

(58) Field of Classification Search
None
See application file for complete search history.

(56) References Cited

U.S. PATENT DOCUMENTS

| 2,854,482 A | 9/1958 | Guyer | |
|---|---|---|---|
| 3,184,508 A * | 5/1965 | Kaasenbrood | C07C 273/16 564/73 |
| 3,185,731 A * | 5/1965 | Kaasenbrood | C07C 273/16 564/73 |
| 3,251,879 A * | 5/1966 | Rosenbloom | C05C 9/005 564/73 |

FOREIGN PATENT DOCUMENTS

GB            1141419 A       1/1969

OTHER PUBLICATIONS

International Search Report issued Feb. 9, 2022 in connection with PCT Application No. PCT/EP2021/082271.
Written Opinion of the International Searching Authority issued Feb. 9, 2022 in connection with PCT Application No. PCT/EP2021/082271.
International Preliminary Report on Patentability issued Mar. 27, 2023 in connection with PCT Application No. PCT/EP2021/082271.

* cited by examiner

*Primary Examiner* — Amy C Bonaparte
(74) *Attorney, Agent, or Firm* — Akerman LLP

(57) ABSTRACT

A process for the production of urea wherein: production of pure urea (U) includes the concentration of an aqueous urea solution (23) by crystallization; a urea crystallization purge aqueous phase (32) comprising urea, water and biuret, which is purged from the urea crystallization process, is used in a high-biuret urea processing section (34) for additional production of urea with a high content of biuret.

13 Claims, 2 Drawing Sheets

PROCESS FOR PRODUCING UREA AND BIURET

CROSS-REFERENCE TO RELATED APPLICATIONS

This application is a national phase of PCT/EP2021/082271, filed Nov. 19, 2021, and claims priority to EP 20214560.3, filed Dec. 16, 2020, the entire contents of both of which are hereby incorporated by reference.

FIELD OF THE INVENTION

The invention relates to production of urea including crystallization.

PRIOR ART

Urea is produced industrially by reacting ammonia and carbon dioxide at suitable urea-forming conditions, typically at a high pressure and high temperature.

Urea is synthesized at a synthesis pressure above 100 bar obtaining a reaction effluent containing urea, water and unconverted reagents mostly in the form of ammonium carbamate. Due to the equilibrium reached in the reaction environment, the amount of unconverted matter in the reaction effluent is significant and the reaction effluent is normally processed for its recovery.

To this purpose, the reaction effluent is normally processed in a recovery section at a pressure lower than the synthesis pressure, obtaining a recycle solution containing the reagents removed from the effluent, and a purified aqueous solution of urea. Said purified solution typically contains around 65-70% urea, the balance being water and unavoidable impurities.

The process of recovery normally includes heating the solution to decompose ammonium carbamate and remove a gaseous phase containing ammonia and carbon dioxide, and condensing said gaseous phase to obtain a recycle solution.

In the widely used stripping processes, the effluent of a high-pressure reactor is heated in a high-pressure stripper, possibly in the presence of a stripping agent, to decompose the ammonium carbamate and extract gaseous ammonia and carbon dioxide. These are condensed in a high-pressure condenser and recycled to the synthesis reactor. When used, the stripping agent is generally gaseous carbon dioxide or gaseous ammonia.

Said high-pressure stripper and high-pressure condenser may operate at substantially the same pressure as the synthesis reactor, thus forming a high-pressure synthesis section or loop. The urea-containing effluent of the stripper is then processed in one or more recovery sections as described above.

The impurities found in the purified solution normally include biuret. Urea is subject to thermal decomposition into biuret and ammonia and therefore some biuret may inevitably form in the process. In the conventional production of urea, biuret is an undesired by-product and efforts are made to avoid its formation. Most applications of urea, such as fertilizer-grade urea or technical-grade urea, require a content of biuret not greater than 1.0% by weight.

Many applications require urea in a solid form. The production of solid urea is also termed finishing or product-shaping. The known shaping processes like granulation or prilling require a highly concentrated urea melt. There is the need, therefore, to remove water from the purified aqueous solution withdrawn from the recovery section. Water can be removed for example by evaporation or crystallization.

It is well known in the art that the crystallization process, compared to the evaporation process, allows to produce urea with much lower content of biuret. Typically, less than 0.9% wt (% by weight) preferably less than 0.6% wt end more preferably less than 0.3% wt biuret can be achieved with crystallization. If kept below the saturation point in the urea solution, the biuret does not crystallize together with urea but remains in the liquid. Urea with such low content of biuret is named urea low biuret—LBU and is required for specific purposes such as solutions for catalytic removal of NOx from exhaust gas (known as diesel exhaust fluid or DEF), foliar grade fertilizers and others. The DEF is typically an aqueous solution of urea containing 32.5% wt of urea. Quality requirements for DEF can be found in the DIN 70070 Norm.

In a crystallization process, the urea solution is heated and depressurized to vacuum, typically around 0.1 bar abs, so that water evaporates from the solution. The temperature of crystallization may be for example 55° C. to 100° C. Urea crystals are produced by the crystallization and separated from the aqueous phase (mother liquor) by suitable means, such as a combination of sieve bends and centrifuges. The crystals are then melted for shaping in a suitable device such as a prilling tower or granulation unit.

The mother liquor of the crystallization process typically has a relevant content of biuret due to the different solubility of biuret and urea in water. The amount of biuret in the mother liquor may be around 10% by weight. In a typical case, the crystallization mother liquor may contain (in weight) about 63% urea, 27% water and 10% biuret.

Part of the crystallization mother liquor is normally recycled internally in the crystallization process. However a portion of this mother liquor must be purged to avoid accumulation of biuret above the saturation level and its precipitation.

Precipitation of biuret is undesired because it would contaminate the solid urea and reduce its market price. For example a stream of mother liquor is purged from a centrifuge where crystals of urea are separated. By purging some of the liquor, the concentration of biuret in the centrifuge is kept above the saturation level and precipitation of biuret is prevented.

The urea crystallization purge aqueous phase is typically recycled to the urea reactor.

A drawback of the above technique is the recycle to the urea reactor of a stream containing urea and water. Both urea and water are reaction products and introducing urea and water into the reaction environment shifts the equilibrium opposite to the formation of urea, thus affecting the performance of the reactor.

Therefore in the prior art of urea plants using crystallization to remove water the skilled person is faced with two possibilities: either the crystallization purge stream is recycled to the reactor, which affects the conversion, or the precipitation of biuret together with the crystals of urea is accepted, which would downgrade the urea product. Clearly, neither of these options is fully satisfactory and there would be an incentive to find another solution.

SUMMARY OF THE INVENTION

The invention faces the problem of how to deal with the crystallization purge stream of mother liquor of a urea plant without causing a contamination of the urea or affecting the performance of the urea synthesis reactor. The above problem is solved with a process according to claim 1.

In the invention, the crystallization mother liquor is processed in a separate section for the production of an additional valuable product, which is urea with a high content of biuret. Although considered an impurity in the urea production, biuret is a valuable product for certain applications. For example biuret is a useful source of non-protein nitrogen (NPN) for cattle feed.

The current production of biuret from urea involves basically dissolving the commercial solid urea to form a urea melt, and maintaining the so obtained melt in a batch reactor at a suitable temperature around 160° C., deep vacuum and for a suitable residence time for thermal decomposition of urea. The invention provides a novel process for the production of urea with a high content of biuret, termed high-biuret urea, whose production is integrated with the production of low-biuret urea.

The integration of the production of biuret with the conventional production of low-biuret urea (LBU) is an interesting feature of the invention. The term low-biuret urea denotes urea for uses wherein biuret is a strongly undesired by-product. The content of biuret in the LBU is typically not greater than 0.9%, preferably not greater than 0.6 and more desirably not greater than 0.3% by weight.

The invention has the following advantages: the detrimental recycle of urea and water to the urea synthesis reactor can be reduced or fully eliminated; an efficient production of valuable low-biuret urea such as foliar grade fertilizer urea is combined with a concomitant production of another valuable product. It can be said the invention provides a way for the processing of the waste aqueous phase discharged by the crystallization of urea, thus obtaining a valuable product from a stream which in the prior art was simply regarded as a waste.

The high-biuret urea can be produced without additives typically used in the urea shaping process, notably formaldehyde. This is a further advantage of the invention because formaldehyde is not desired in many applications of biuret, particularly for cattle feed, because formaldehyde poses serious health concerns.

Further aspects of the invention include a plant and a method of modifying a urea plant according to the claims.

The invention can be applied to all processes for the production of urea including in particular the total-recycle process and the stripping process. The stripping process may be CO2-stripping or ammonia-stripping or self-stripping. All these processes are known to a skilled person and described in the literature.

DESCRIPTION OF THE INVENTION

The high-biuret urea, which is obtained from processing the waste aqueous phase from urea crystallization, may contain at least 55% by weight of biuret, preferably at least 70% by weight. The balance is predominantly composed of urea and water. Preferably the sum of biuret and urea in the high-biuret urea is at least 80% by weight. In the various embodiments of the invention, the high-biuret urea may be in the form of granules or powder.

The high-biuret urea is produced in a dedicated high-biuret urea processing section. The processing of the urea crystallization aqueous phase in this processing section may include a step of crystallization arranged to produce crystals containing urea and biuret. It has to be noted this step of crystallization for the production of high-biuret urea is separate from the crystallization of urea and is performed in a separate crystallization section.

The urea crystallization purge aqueous phase is diluted with water before or during the processing in the high-biuret urea processing section. The desired water concentration after dilution is about 50% wt.

The crystallization for the production of high-biuret urea is performed by cooling the aqueous phase to a suitable temperature.

The crystallization typically produced a slurry containing precipitated crystals and a mother liquor. The crystals may be separated from the slurry in a suitable device such as a centrifuge. After separation of the crystals from the slurry, the process of production of the high-biuret urea may further include a removal of water from the crystals.

The urea crystallization aqueous phase, which is the source material for the production of the high-biuret urea, contains preferably at least 5% by weight of biuret, preferably at least 10% by weight. In a typical case said urea crystallization aqueous phase contains by weight 50% to 65% urea, 5% to 20% biuret, the balance being water and unavoidable impurities. For example said aqueous phase contains by weight about 63% urea, about 27% water and about 10% biuret (all % are by weight).

As stated above, the invention is applicable to various processes for production of urea. In a typical embodiment urea is produced at a high pressure of synthesis in a urea synthesis section, obtaining a synthesis effluent containing urea, water and unconverted ammonium carbamate; said effluent is processed in a recovery section at one or more pressure levels lower than the synthesis pressure to recover unconverted reagents which are recycled to the synthesis section, and said aqueous solution is obtained in the recovery section.

Particularly preferably, all the aqueous phase withdrawn from the urea crystallization section is sent to the high-biuret urea processing section and no part of such aqueous phase is recycled to the urea synthesis section. Hence the above discussed disadvantage of introducing urea and water in the reactor is fully avoided.

The production of the high-biuret urea releases a residual aqueous phase. This aqueous phase may be for example the mother liquor of a crystallization process, after separation of the urea and biuret crystals. Said mother liquor may contain about 3% of biuret by weight.

In a preferred embodiment said residual aqueous phase is recycled to the urea crystallization section. Preferably said aqueous phase is mixed with the urea solution withdrawn from the urea recovery section.

A plant for implementing the process of the invention comprises:
  a urea crystallization section arranged to process an aqueous urea solution and to obtain solid crystals of urea and a urea crystallization aqueous phase comprising urea, water and biuret;
  a processing section and a line arranged to feed waste water separated in the urea crystallization section to said processing section;
  the processing section being arranged to obtain, from said aqueous phase, a high-biuret urea in the form of a solid product made predominantly of biuret and urea.

A urea plant including a crystallization section may be modified by adding a processing section suitable for the production of high-biuret urea, as described above. The modification further includes the provision of a line arranged to feed the urea crystallization aqueous phase to said newly-added processing section.

An existing line for recycling a crystallization waste aqueous phase to the reactor, if present, may be discontinued to the benefit of the efficiency of conversion in the reactor. Hence the invention applied to a urea plant can make the plant more efficient in terms of urea conversion and, at the same time, adapted to deliver a further added-value product, that is the biuret.

DESCRIPTION OF THE FIGURES

The invention and its advantages are now elucidated with the help of the figures wherein.

Figure 1:
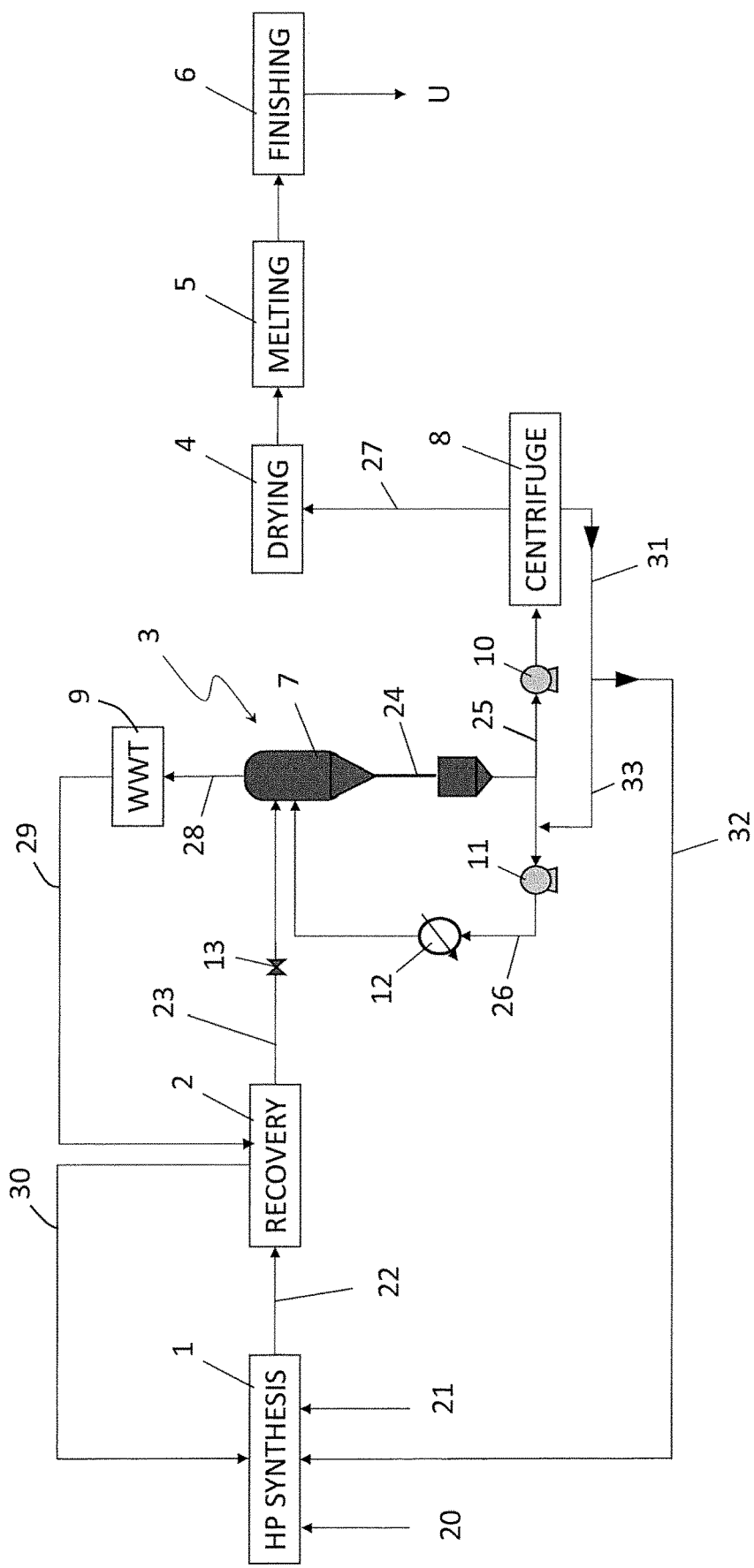
FIG. 1 illustrates a prior art urea production process involving crystallization.

The process and items depicted in FIG. 1 are familiar to a skilled person. Fresh carbon dioxide 20 and ammonia 21 are reacted in the synthesis section 1 at a high pressure, e.g. above 100 bar, to form a reaction effluent 22 containing urea, water and unconverted reagent mostly in the form of ammonium carbamate.

Said effluent 22 is processed in the recovery section 2 at a lower pressure, for example in a low-pressure stage or in a medium-pressure stage followed by a low-pressure stage. Here the solution is heated to decompose the ammonium carbamate and gaseous ammonia and carbon dioxide removed for the solution are condensed to form a recycle solution 30 sent back to the synthesis section 1.

The recovery section 2 produces an aqueous solution 23 made predominantly of urea and water which after de-pressurization in a valve 13 is sent to the crystallization section 3.

A crystallizer 7 removes water from the solution and forms a stream 24 containing crystals of urea and an aqueous phase (mother liquor). The water 28 removed in the crystallizer 7 is sent to a waste water treatment unit 9 and forms a carbonate-containing stream 29 which can be recycled to the recovery section 2.

A portion 25 of said stream of crystals and liquor is sent via pump 10 to a centrifuge 8. Another portion 26 of the effluent of the crystallizer is recycled via line 26, pump 11 and heat exchanger 12.

In the centrifuge 8 solid crystals of urea 27 are separated from the liquor. The crystals are further dried in a drying unit 4 and melted in a melting unit 5. The so obtained pure urea melt feeds a finishing section 6 such as a prilling tower or a granulator where urea U is produced.

The urea U is a low-biuret urea, containing for example less than 0.9% or less than 0.6% of biuret in weight. Such a low content of biuret is required e.g. for use of the urea in the preparation of a diesel exhaust fluid or for use as foliar grade fertilizer.

The centrifuge 8 separates a stream of a crystallization aqueous phase 31 containing urea, water and biuret. A portion 33 of this liquor is reintroduced in the crystallizer 7 via line 26; a purge stream 32 is separated to avoid accumulation and precipitation of biuret. This stream 32 represents a waste of the urea crystallization process. FIG. 1 illustrates the aqueous purge stream 32 is sent to the synthesis section 1, which is common in the prior art but, as explained above, negatively affects the efficiency of conversion in the urea reactor.

Figure 2:
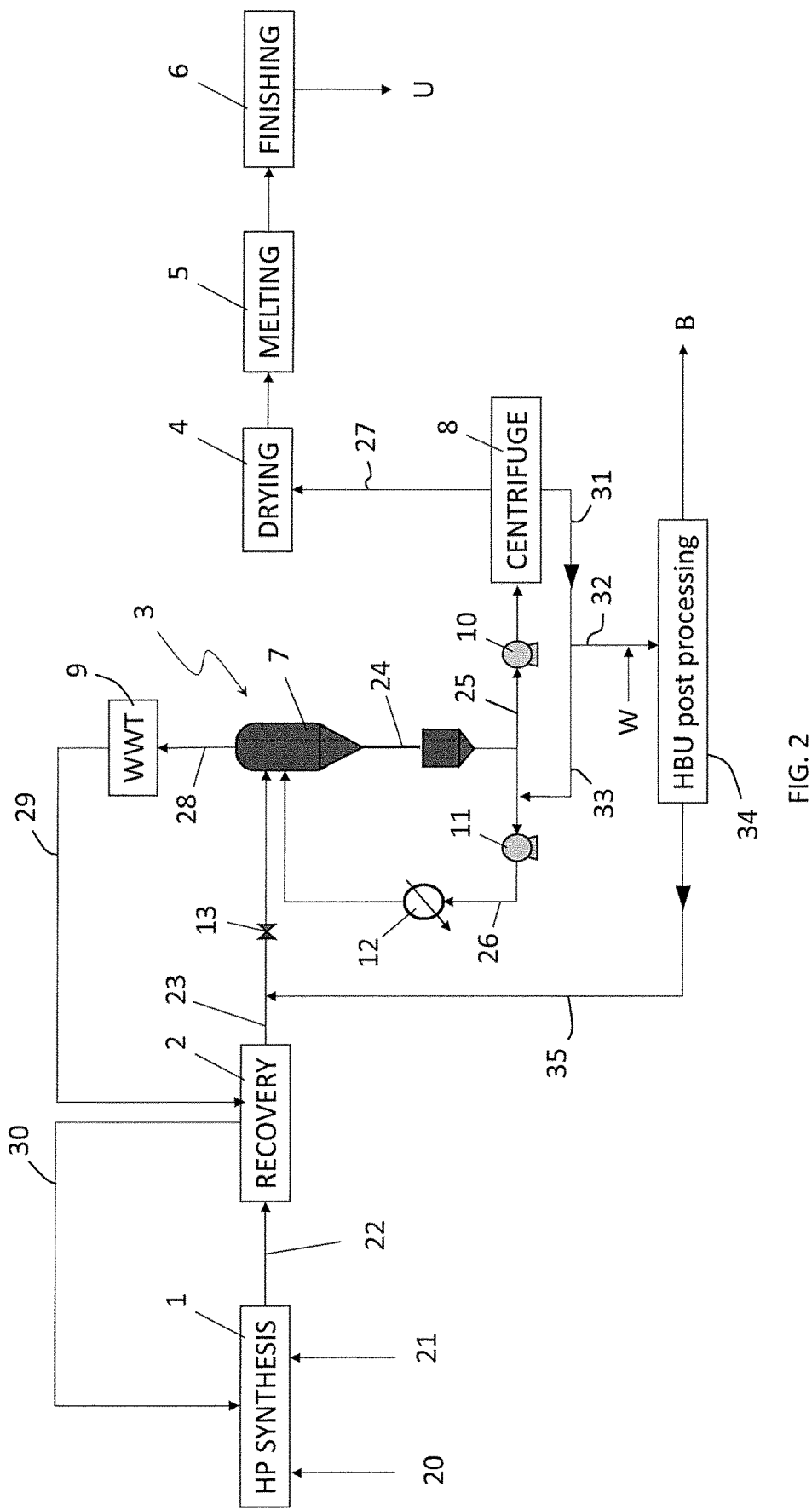
FIG. 2 illustrates the production process of FIG. 1 modified according to the invention for the integrated production of conventional urea and high-biuret urea.

FIG. 2 illustrates the plant modified in accordance with the invention. The crystallization waste stream 32 is sent to a high-biuret urea post-processing section 34 after dilution with water W.

In the section 34, a process of crystallization is performed. Said crystallization process produces a slurry including precipitated solid phase and a mother liquor.

The slurry is processed to separate the solid phase which may be dried to obtain high-biuret urea B. The remaining mother liquor 35 is recycled to the crystallization section 3, for example with the urea solution 23. It can be seen that the invention avoids contamination of the synthesis section 1 with biuret or urea.

EXAMPLE

In a urea plant with a capacity of 790 metric tons per day, 33,000 kg/h of a urea solution (line 23) are sent to the urea crystallization section. Said solution is at 90 C.° and contains 71.64% urea; 0.36% biuret; 28% water by weight. The crystallization in the section 3 is performed at 0.1 bar absolute pressure and about ° C.

1520 kg/h of crystallization aqueous phase are removed with the purge line 32. This amount is regulated to keep a concentration of biuret not greater than 10%. The composition of the centrifuge mother liquor of line 31 is 63% urea, 27% water and 10% biuret.

The purge stream 32 is added with 1310 kg/h of water for dilution. In the processing section 34, 165 kg/h of solid high-biuret urea are obtained. The line 35 carries 3,990 kg/h of a residual mother liquor at about 3% of biuret.

What is claimed is:

1. A process for the production of urea, the process comprising:
concentrating an aqueous urea solution by crystallization in a crystallization section to produce solid crystals of urea and a urea crystallization purge aqueous phase comprising urea, water and biuret;
purging the urea crystallization purge aqueous phase from the crystallization process; and
further processing at least a portion of said urea crystallization purge aqueous phase in a high-biuret urea processing section to produce a high-biuret urea in a solid form, wherein the high-biuret urea comprises at least 55% by weight of biuret;
wherein urea is produced at a high pressure of synthesis in a urea synthesis section, obtaining a synthesis effluent;
said effluent is processed in a recovery section at one or more pressure levels lower than the synthesis pressure to recover unconverted reagents which are recycled to the synthesis section, and said aqueous urea solution is obtained in the recovery section.

2. The process according to claim 1, wherein said high-biuret urea contains at least 70% by weight of biuret.

3. The process according to claim 1, wherein the sum of biuret and urea in the high-biuret urea is at least 80% by weight.

4. The process according to claim 1, wherein the urea crystallization purge aqueous phase is diluted with water before or during the processing in the high-biuret urea processing section.

5. The process according to claim 1, wherein the processing of the urea crystallization purge aqueous phase in the high-biuret urea processing section further includes a step of crystallization wherein solid crystals containing biuret and urea are obtained.

6. The process according to claim 5, wherein processing in the high-biuret urea processing section further includes separation of the crystals from a crystallization slurry and further processing of said crystals to remove residual water and obtain said high-biuret urea.

7. The process according to claim 1, wherein said urea crystallization purge aqueous phase contains at least 5% by weight of biuret.

8. The process according to claim 1, wherein said urea crystallization purge aqueous phase contains by weight 50% to 65% urea, 5% to 20% biuret, the balance being water and impurities.

9. The process according to claim 1, wherein all of the urea crystallization purge aqueous phase produced in the urea crystallization section is sent to the high-biuret urea processing section and no part of said urea crystallization purge aqueous phase is reintroduced into the urea synthesis section.

10. The process according to claim 1, further comprising:
withdrawing a residual aqueous phase from the high-biuret urea processing section; and
recycling said residual aqueous phase to the urea crystallization section.

11. A plant for producing pure urea and high-biuret urea with a process in accordance with claim 1, the plant comprising:
a high-pressure urea synthesis section to obtain a synthesis effluent;
a recovery section connected to the urea synthesis section, the recovery section arranged to process said synthesis effluent at one or more pressure levels lower than the synthesis pressure to recover unconverted reagents and arranged to recycle said unconverted reagents to said urea synthesis section, and to obtain an aqueous urea solution;
a urea crystallization section arranged to process said aqueous urea solution and to obtain solid crystals of urea and a urea crystallization purge aqueous phase comprising urea, water and biuret;
a processing section and a line arranged to feed a said urea crystallization purge aqueous phase separated in the urea crystallization section to said processing section;
the processing section being arranged to obtain, from said urea crystallization purge aqueous phase, a high-biuret urea in a solid form;
wherein said processing section includes a crystallization section arranged to produce crystals containing biuret and a centrifuge arranged to separate the crystals from a crystallization mother liquor.

12. A method of modifying a urea plant, wherein:
the plant includes a urea crystallization section arranged to produce solid urea by crystallization of an aqueous urea solution, to obtain solid crystals of urea and a crystallization aqueous phase comprising urea, water and biuret;
the method including:
adding a processing section to the plant, wherein the processing section is arranged to obtain, from said aqueous phase, a high-biuret urea in the form of a solid product made predominantly of biuret and urea;
providing a line to feed part or all of the crystallization aqueous phase withdrawn from the urea crystallization section to the newly-installed processing section for the production of high-biuret urea;
said modified urea plant comprising:
a high-pressure urea synthesis section to obtain a synthesis effluent;
a recovery section arranged to process said synthesis effluent at one or more pressure levels lower than the synthesis pressure to recover unconverted reagents and arranged to recycle said unconverted reagents to said urea synthesis section, and to obtain an aqueous urea solution;
a urea crystallization section arranged to process said aqueous urea solution and to obtain solid crystals of urea and a urea crystallization purge aqueous phase comprising urea, water and biuret;
a processing section and a line arranged to feed a said urea crystallization purge aqueous phase separated in the urea crystallization section to said processing section;
the processing section being arranged to obtain, from said urea crystallization purge aqueous phase, a high-biuret urea in a solid form;
wherein said processing section includes a crystallization section arranged to produce crystals containing biuret and a centrifuge arranged to separate the crystals from a crystallization mother liquor.

13. The process according to claim 1, wherein said urea crystallization purge aqueous phase contains at least 10% by weight of biuret.

* * * * *